(12) United States Patent
Harding

(10) Patent No.: US 7,697,664 B2
(45) Date of Patent: Apr. 13, 2010

(54) SYSTEMS AND METHODS FOR DETERMINING AN ATOMIC NUMBER OF A SUBSTANCE

(75) Inventor: Geoffrey Harding, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 145 days.

(21) Appl. No.: 11/434,431

(22) Filed: May 15, 2006

(65) Prior Publication Data

US 2007/0263771 A1 Nov. 15, 2007

(51) Int. Cl.
*G01N 23/20* (2006.01)
*G01T 1/36* (2006.01)

(52) U.S. Cl. .......................................... 378/71; 378/83
(58) Field of Classification Search .................. 378/57, 378/70–78, 82–90, 901
See application file for complete search history.

(56) References Cited

U.S. PATENT DOCUMENTS

| | | | | |
|---|---|---|---|---|
| 4,754,469 A * | 6/1988 | Harding et al. | ............... | 378/88 |
| 4,887,285 A * | 12/1989 | Harding et al. | ............... | 378/88 |
| 5,265,144 A | 11/1993 | Harding et al. | | |
| 5,428,657 A * | 6/1995 | Papanicolopoulos et al. | .. | 378/86 |
| 5,600,303 A | 2/1997 | Husseiny et al. | | |
| 5,612,988 A * | 3/1997 | Martens | ........................ | 378/86 |
| 5,812,630 A * | 9/1998 | Blaffert | ........................ | 378/83 |
| 6,442,233 B1 | 8/2002 | Grodzins et al. | | |
| 6,744,845 B2 * | 6/2004 | Harding et al. | ............... | 378/16 |
| 6,751,288 B1 * | 6/2004 | Hessler | ........................ | 378/86 |
| 2001/0021241 A1 | 9/2001 | Swift et al. | | |
| 2003/0091147 A1 * | 5/2003 | Takata et al. | .................. | 378/71 |
| 2006/0140340 A1 * | 6/2006 | Kravis | ........................... | 378/57 |

FOREIGN PATENT DOCUMENTS

EP 0462658 A 12/1991
WO 2006010056 A 1/2006

OTHER PUBLICATIONS

U.S. Appl. No. 11/504,263, filed Aug. 15, 2006, Geoffrey Harding.
U.S. Appl. No. 11/498,114, filed Aug. 2, 2006, Geoffrey Harding.
U.S. Appl. No. 11/498,113, filed Aug. 2, 2006, Geoffrey Harding.
U.S. Appl. No. 11/484,186, filed Jul. 11, 2006, Geoffrey Harding.
U.S. Appl. No. 11/416,526, filed May 3, 2006, Geoffrey Harding et al.
U.S. Appl. No. 11/541,716, filed Sep. 29, 2006, Geoffrey Harding.
U.S. Appl. No. 11/531,019, filed Sep. 12, 2006, Geoffrey Harding.

(Continued)

*Primary Examiner*—Edward J Glick
*Assistant Examiner*—Anastasia Midkiff
(74) *Attorney, Agent, or Firm*—Armstrong Teasdale LLP

(57) ABSTRACT

A method for determining a type of substance is described. The method includes determining an effective atomic number of the substance based on a measured ratio of numbers of detected x-ray scatter photons in a diffraction profile.

20 Claims, 5 Drawing Sheets

OTHER PUBLICATIONS

U.S. Appl. No. 11/434,486, filed May 15, 2006, Geoffrey Harding.
U.S. Appl. No. 11/434,291, filed May 15, 2006, Geoffrey Harding.
U.S. Appl. No. 11/504,395, filed Aug. 15, 2006, Geoffrey Harding.
U.S. Appl. No. 11/531,037, filed Sep. 12, 2006, Geoffrey Harding.
Hubbell, J.H., Veigele, W.J., Briggs, E.A., Brown, R.T., Cromer, D.T., Howerton, R.J., "Atomic Form Factors, Incoherent Scattering Functions and Photon Scattering Cross-sections," Journal of Physics and Chemical Reference Data, vol. 4, No. 3, pp. 471-538 (1975).
Hubbell, J.H., Veigele, W.J., Briggs, E.A., Brown, R.T., Cromer, D.T., Howerton, R.J., "Erratum; Atomic Form Factors, Incoherent Scattering Functions, and Photon Scattering Cross Sections," Journal of Physics and Chemical Reference Data, vol. 6, pp. 615-616 (1977).
Schlomka et al., "Coherent Scatter Computer Tomography—A Novel Medical Imaging Technique," Physics of Medical Imaging, Proceedings of SPIE—vol. 5030, pp. 256-265 (2003).
Rabiej M., "Determination of the Degree of Crystallinity of Semicrystalline Polymers by Means of the 'OptiFit' Computer Software," Polimery 6, pp. 423-427 (2002).
"Percentage Crystallinity Determination by X-Ray Diffraction," XRD-6000 Application Brief, Kratos Analytical—A Shimadzu Group Company, pp. 1-5 (1999).
A.M. Hindeleh and D. J. Johnson, "The Resolution of Multipeak Data in Fibre Science," J. Phys. D: Appl. Phys., vol. 4. Printed in Great Britain, pp. 259-263 (1971).
D.J. Garrity, Transmission Geometry X-Ray Diffraction for Materials Research, University of Surrey—Year Reviews, 2005, XP002485496, 86 pages.
Patent cooperation Treaty International Search Report, for International Application No. PCT/US2007/066846, dated Apr. 18, 2007.

* cited by examiner

SYSTEMS AND METHODS FOR DETERMINING AN ATOMIC NUMBER OF A SUBSTANCE

BACKGROUND OF THE INVENTION

This invention relates generally to systems and methods for determining a type of substance and more particularly to systems and methods for determining an atomic number of the substance.

The events of Sep. 11, 2001 instigated an urgency for more effective and stringent screening of airport baggage. The urgency for security expanded from an inspection of carry-on bags for knives and guns to a complete inspection of checked bags for a range of hazards with particular emphasis upon concealed explosives. X-ray imaging is a widespread technology currently employed for screening. However, existing x-ray baggage scanners, including computed tomography (CT) systems, designed for detection of explosive and illegal substances are unable to discriminate between harmless materials in certain ranges of density and threat materials like plastic explosive.

A plurality of identification systems based on a plurality of x-ray diffraction (XRD) techniques provide an improved discrimination of materials compared to that provided by the x-ray baggage scanners. The XRD identification systems measure a plurality of d-spacings between a plurality of lattice planes of micro-crystals in materials.

However, the XRD identification systems for explosives detection and baggage scanning are not yet highly developed. Moreover, the diffraction techniques suffer from a false alarm problem for some classes of substances. There are certain types of explosives in which an explosive component cannot be identified by the XRD identification systems and the lack of identification leads to a high false alarm rate.

BRIEF DESCRIPTION OF THE INVENTION

In an aspect, a method for determining a type of substance is described. The method includes determining an effective atomic number of the substance based on a measured ratio of numbers of detected x-ray scatter photons in a diffraction profile.

In another aspect, a processor for determining a type of substance is described. The processor is configured to determine an effective atomic number of the substance based on a measured ratio of numbers of detected x-ray scatter photons in a diffraction profile.

In yet another aspect, a system for determining a type of substance is described. The system includes an x-ray source configured to generate x-rays, a detector configured to detect primary and coherent scatter after the x-rays pass through the substance, and a processor configured to determine an effective atomic number of the substance based on a measured ratio of numbers of detected x-ray scatter photons in a diffraction profile.

DETAILED DESCRIPTION OF THE INVENTION

Figure 1:
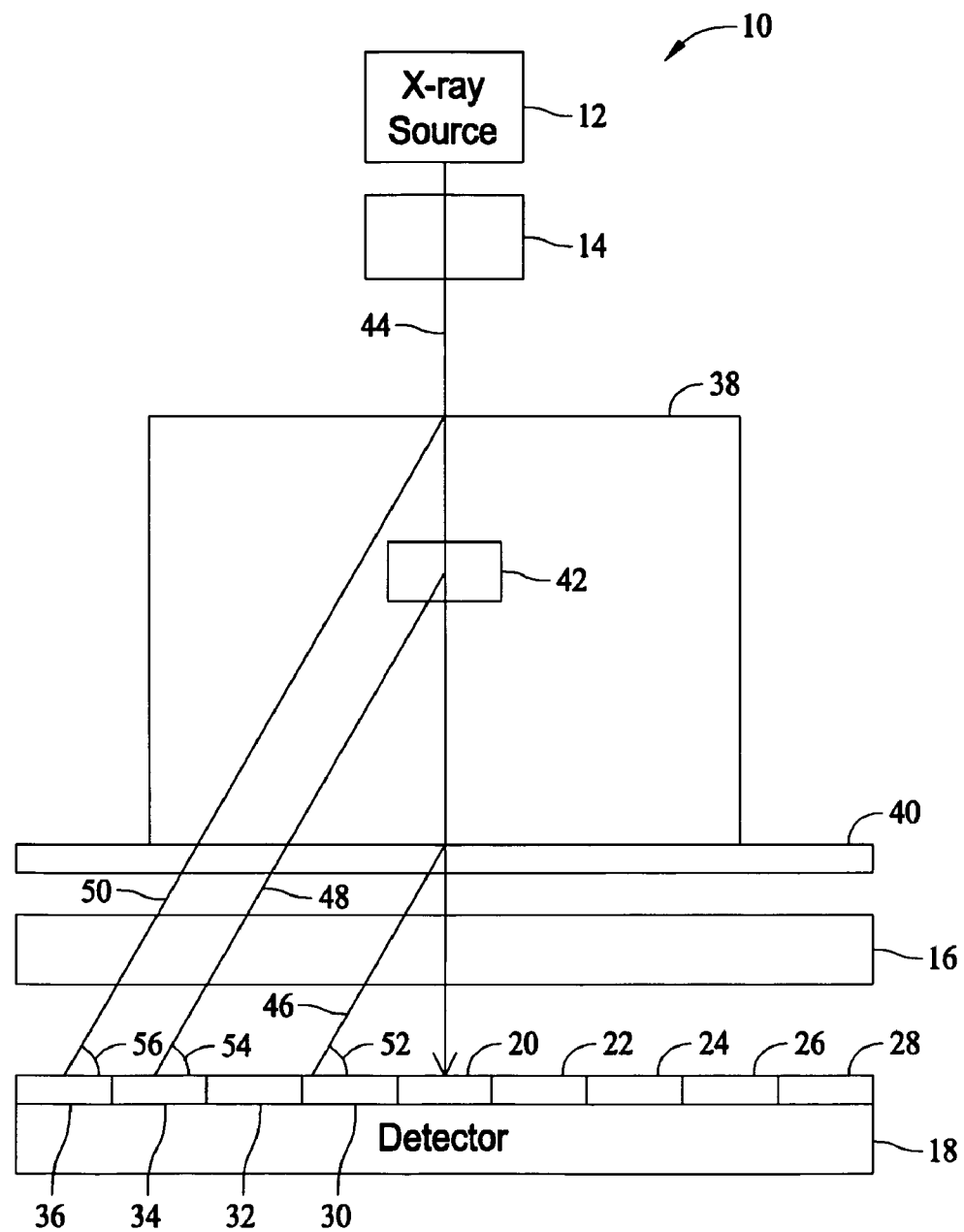
FIG. 1 is a block diagram of a system for determining an atomic number of a substance.

FIG. 1 is a block diagram of a system 10 for determining an atomic number of a substance. System 10 includes an x-ray source 12, a primary collimator 14, a secondary collimator (Sec collimator) 16, and a detector 18. Detector 18 includes a central detector element 20 or a central detector cell for detecting primary radiation. Detector 18 also includes a plurality of detector cells or detector elements 22, 24, 26, 28, 30, 32, 34, and 36 for detecting coherent scatter. Detector 18 includes any number, such as, ranging from and including 256 to 1024, of detector elements. A container 38 is placed on a support 40 between x-ray source 12 and detector 18. Examples of container 38 include a bag, a box, and an air cargo container. Examples of x-ray source 12 include a polychromatic x-ray tube. Container 38 includes a substance 42. Examples of substance 42 include an organic explosive, an amorphous substance having a crystallinity of less than twenty five percent, a quasi-amorphous substance having a crystallinity at least equal to twenty-five percent and less than fifty percent, and a partially crystalline substance having a crystallinity at least equal to fifty percent and less than one-hundred percent. Examples of the amorphous, quasi-amorphous, and partially crystalline substances include a gel explosive, a slurry explosive, an explosive including ammonium nitrate, and a special nuclear material. Examples of the special nuclear material include plutonium and uranium. Examples of support 40 include a table and a conveyor belt. An example of detector 18 includes a segmented detector fabricated from Germanium.

X-ray source 12 emits x-rays in an energy range, which is dependent on a voltage applied by a power source to x-ray source 12. Using primary collimator 14, a primary beam 44, such as a pencil beam, is formed from the x-rays generated. Primary beam 44 passes through container 38 arranged on support 40 to generate scattered radiation, such as a plurality of scattered rays 46, 48, and 50. Underneath support 40, there is arranged detector 18, which measures an intensity of primary beam 44 and photon energy of the scattered radiation. Detector 18 measures the x-rays in an energy-sensitive manner by outputting a plurality of electrical output signals linearly dependent on a plurality of energies of x-ray quanta detected from within primary beam 44 and the scattered radiation.

Detector elements 20, 22, 24, 26, 28, 30, 32, 34, and 36 are geometrically arranged so that a scatter angle or alternatively an incident angle of the scatter radiation detected by each detector element 20, 22, 24, 26, 28, 30, 32, 34, and 36 is constant. For example, an incident angle 52 at which scattered ray 46 is incident on detector element 30 is equal to an incident angle 54 at which scattered ray 48 is incident on detector element 34 and incident angle 54 is equal to an incident angle 56 at which scattered ray 50 is incident on detector element 36. As another example, scattered ray 46 is parallel to scattered rays 48 and 50. Central detector element 20 measures an energy or alternatively an intensity of primary beam 44 after primary beam 44 passes through container 38. Detector elements 22, 24, 26, 28, 30, 32, 34, and 36 separately detect the scattered radiation received from container 38.

Secondary collimator 16 is located between support 40 and detector 18. Secondary collimator 16 includes a number of collimator elements, such as sheets, slits, or laminations, to ensure that the scatter radiation arriving at detector 18 have constant scatter angles with respect to primary beam 44 and that a position of detector 18 permits a depth in container 38 at which the scatter radiation originated to be determined. The number of collimator elements provided is equal to or alternatively greater than a number of detector elements 20, 22, 24, 26, 28, 30, 32, 34, and 36 and the collimator elements are arranged such that the scattered radiation between neighboring collimator elements each time is incident on one of the detector elements 22, 24, 26, 28, 30, 32, 34, and 36. The collimator elements are made of a radiation-absorbing material, such as, a copper alloy or a silver alloy. In one embodiment employing a fan-beam geometry, a plurality of origination points, within container 38, of the scatter radiation are detected by the detector elements 22, 24, 26, and 28, that are aligned in a first direction and detector elements 30, 32, 34, and 36 that are aligned in a second direction opposite to and parallel to the first direction. Examples of the constant scatter angle values include values ranging from 0.1 degrees for a high-energy device, such as an x-ray tube radiating x-ray photons having an energy of 1 mega electronvolts (MeV) to four degrees for low-energy systems, such as an x-ray tube radiating x-ray photons having an energy of 150 kilo electronvolts (keV). Detector 18 detects the scattered radiation to generate a plurality of electrical output signals. In an alternative embodiment, system 10 does not include primary and secondary collimators 14 and 16.

Figure 2:
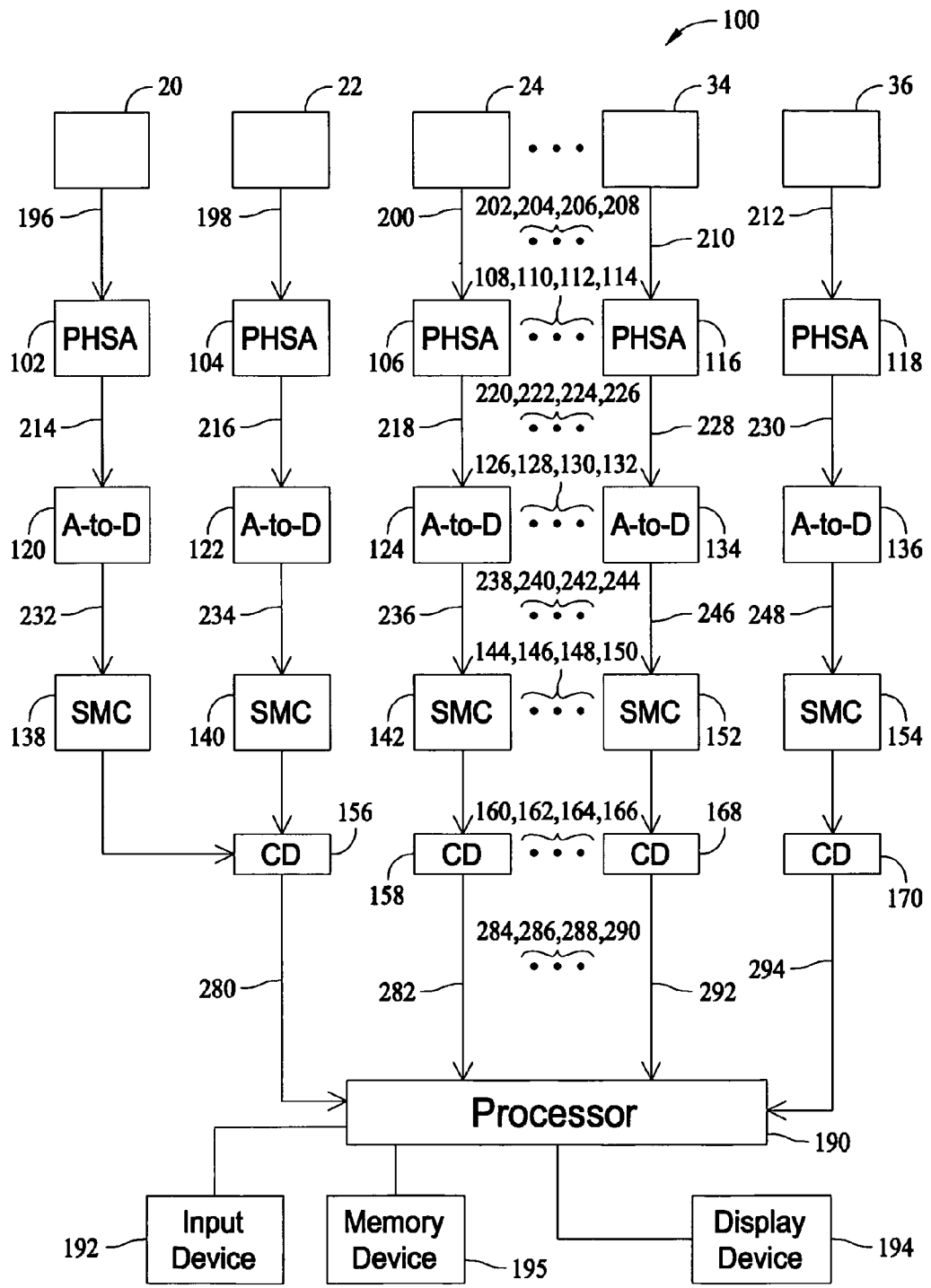
FIG. 2 is a block diagram of an embodiment of the system of FIG. 1.

FIG. 2 is a block diagram of an embodiment of a system 100 for determining an atomic number of a substance 42. System 100 includes central detector element 20, detector elements 22, 24, 26, 28, 30, 32, 34, and 36, a plurality of pulse-height shaper amplifiers (PHSA) 102, 104, 106, 108, 110, 112, 114, 116, and 118, a plurality of analog-to-digital (A-to-D) converters 120, 122, 124, 126, 128, 130, 132, 134, and 136, a plurality of spectrum memory circuits (SMCs) 138, 140, 142, 144, 146, 148, 150, 152, and 154 allowing pulse height spectra to be acquired, a plurality of correction devices (CDs) 156, 158, 160, 162, 164, 166, 168, and 170, a processor 190, an input device 192, a display device 194, and a memory device 195. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer may include a device, such as, a floppy disk drive or CD-ROM drive, for reading data including the methods for determining an atomic number of a substance from a computer-readable medium, such as a floppy disk, a compact disc-read only memory (CD-ROM), a magneto-optical disk (MOD), or a digital versatile disc (DVD). In another embodiment, processor 190 executes instructions stored in firmware. Examples of display device 194 include a liquid crystal display (LCD) and a cathode ray tube (CRT). Examples of input device 192 include a mouse and a keyboard. Examples of memory device 195 include a random access memory (RAM) and a read-only memory (ROM). An example of each of correction devices 156, 158, 160, 162, 164, 166, 168, and 170 include a divider circuit. Each of spectrum memory circuits 138, 140, 142, 144, 146, 148, 150, 152, and 154 include an adder and a memory device, such as a RAM or a ROM.

Central detector element 20 is coupled to pulse-height shaper amplifier 102, and detector elements 22, 24, 26, 28, 30, 32, 34, and 36 are coupled to pulse-height shaper amplifiers 104, 106, 108, 110, 112, 114, 116, and 118, respectively. Central detector element 20 generates an electrical output signal 196 by detecting primary beam 44 and detector elements 22, 24, 26, 28, 30, 32, 34, and 36 generate a plurality of electrical output signals 198, 200, 202, 204, 206, 208, 210, and 212 by detecting the scattered radiation. For example, detector element 22 generates electrical output signal 198 for each scattered x-ray photon incident on detector element 22. Each pulse-height shaper amplifier amplifies an electrical output signal received from a detector element. For example, pulse-height shaper amplifier 102 amplifies electrical output signal 196 and pulse-height shaper amplifier 104 amplifies electrical output signal 198. Pulse-height shaper amplifiers 102, 104, 106, 108, 110, 112, 114, 116, and 118 have a gain factor determined by processor 190.

An amplitude of an electrical output signal output from a detector element is proportional to an integrated intensity of an x-ray quantum that is detected by the detector element to generate the electrical output signal. For example, an amplitude of electrical output signal 196 is proportional to an integrated intensity of an x-ray quantum in primary beam 44 detected by detector element 20. On the other hand, an amplitude of electrical output signal 198 is proportional to an integrated intensity of an x-ray quantum within the scattered radiation that is detected by detector element 22.

A pulse-height shaper amplifier generates an amplified output signal by amplifying an electrical output signal generated from a detector element. For example, pulse-height shaper amplifier 102 generates an amplified output signal 214 by amplifying electrical output signal 196 and pulse-height shaper amplifier 104 generates an amplified output signal 216 by amplifying electrical output signal 198. Similarly, a plurality of amplified output signals 218, 220, 222, 224, 226, 228, and 230 are generated. An analog-to-digital converter converts an amplified output signal from an analog form to a digital form to generate a digital output signal. For example, analog-to-digital converter 120 converts amplified output signal 214 from an analog form to a digital format to generate a digital output signal 232. Similarly, a plurality of digital output signals 234, 236, 238, 240, 242, 244, 246, and 248 are generated by analog-to-digital converters 122, 124, 126, 128, 130, 132, 134, and 136, respectively. A digital value of a digital output signal generated by an analog-to-digital converter represents an amplitude of energy or alternatively an amplitude of intensity of a pulse of an amplified output signal. Each pulse is generated by an x-ray quantum, such as an x-ray photon. For example, a digital value of digital output signal 234 output by analog-to-digital converter 122 is a value of an amplitude of a pulse of amplified output signal 216.

An adder of a spectrum memory circuit adds a number of pulses in a digital output signal. For example, when analog-to-digital converter 122 converts a pulse of amplified output signal 216 into digital output signal 234 to determine an amplitude of the pulse of amplified output signal 216, an adder within spectrum memory circuit 140 increments, by one, a value within a memory device of spectrum memory circuit 140. Accordingly, at an end of an x-ray examination of substance 42, a memory device within spectrum memory circuit stores a number of x-ray quanta detected by a detector element. For example, a memory device within spectrum memory circuit 142 stores a number of x-ray photons detected by detector element 24 and each of the x-ray photons has an amplitude of energy or alternatively an amplitude of intensity that is determined by analog-to-digital converter 124.

A correction device receives a number of x-ray quanta that have a range of energies and are stored within a memory device of one of spectrum memory circuits 140, 142, 144, 146, 148, 150, 152, and 154, and divides the number by a number of x-ray quanta having the range of energies received from a memory device of spectrum memory circuit 138. For example, correction device 156 receives a number of x-ray photons having a range of energies from a memory device of spectrum memory circuit 140, and divides the number by a number of x-ray photons having the range received from a memory device of spectrum memory circuit 138. Each correction device outputs a correction output signal that represents a range of energies within x-ray quanta received by a detector element. For example, correction device 156 outputs a correction output signal 280 representing an energy spectrum or alternatively an intensity spectrum within x-ray quanta detected by detector element 22. As another example, correction device 158 outputs correction output signal 282 representing an energy spectrum within x-ray quanta detector element 24. Similarly, a plurality of correction output signals 284, 286, 288, 290, 292, and 294 are generated by correction devices 160, 162, 164, 166, 168, and 170, respectively.

Processor 190 receives correction output signals 280, 282, 284, 286, 288, 290, 292, and 294 to generate a momentum transfer x, measured in inverse nanometers ($nm^{-1}$), from an energy spectrum r(E) of energy E of x-ray quanta within the scattered radiation detected by detector 18. Processor 190 generates the momentum transfer x by applying $$x = (E/hc)\sin(\theta/2) \quad (1)$$

where c is a speed of light, h is Planck's constant, θ represents constant scatter angles of x-ray quanta of the scattered radiation detected by the detector 18. Processor 190 relates the energy E to the momentum transfer x by equation (1). Mechanical dimensions of the secondary collimator 16 define the scatter angle θ. The secondary collimator 16 restricts the scatter radiation that does not have the angle θ. Processor 190 receives the scatter angle θ from a user via input device 192.

It is noted that a number of pulse-height shaper amplifiers 102, 104, 106, 108, 110, 112, 114, 116, and 118 changes with a number of detector elements 20, 22, 24, 26, 28, 30, 32, 34, and 36. For example, five pulse-height shaper amplifiers are used for amplifying signals received from five detector elements. As another example, four pulse-height shaper amplifiers are used for amplifying signals received from four detector elements. Similarly, a number of analog-to-digital converters 120, 122, 124, 126, 128, 130, 132, 134, and 136 changes with a number of detector elements 20, 22, 24, 26, 28, 30, 32, 34, and 36 and a number of spectrum memory circuits 138, 140, 142, 144, 146, 148, 150, 152, and 154 changes with the number of detector elements 20, 22, 24, 26, 28, 30, 32, 34, and 36.

Figure 3:
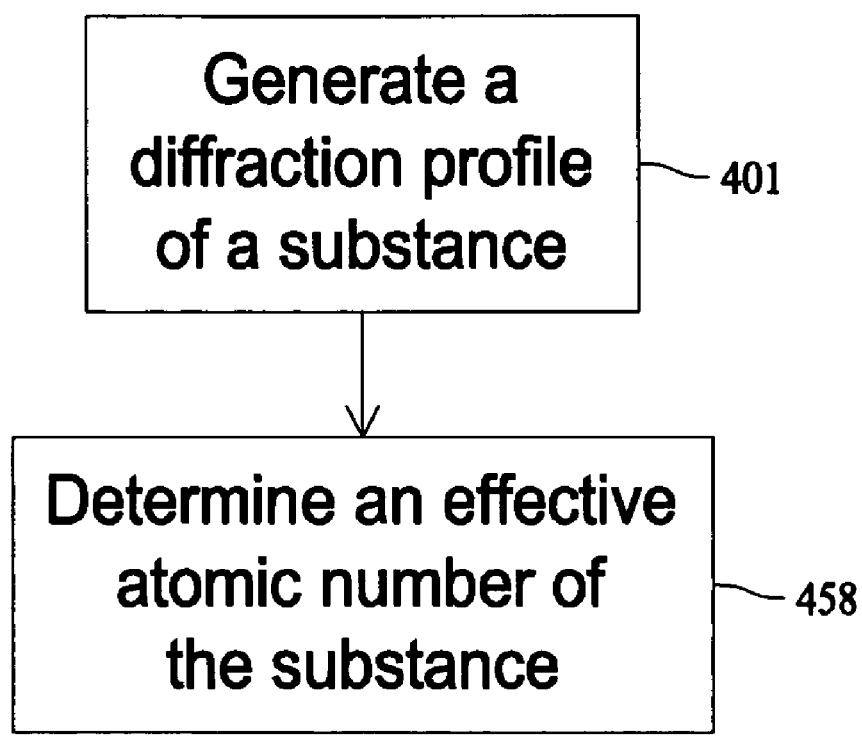
FIG. 3 is a flowchart of an embodiment of a method for determining an atomic number of a substance.
Figure 4:
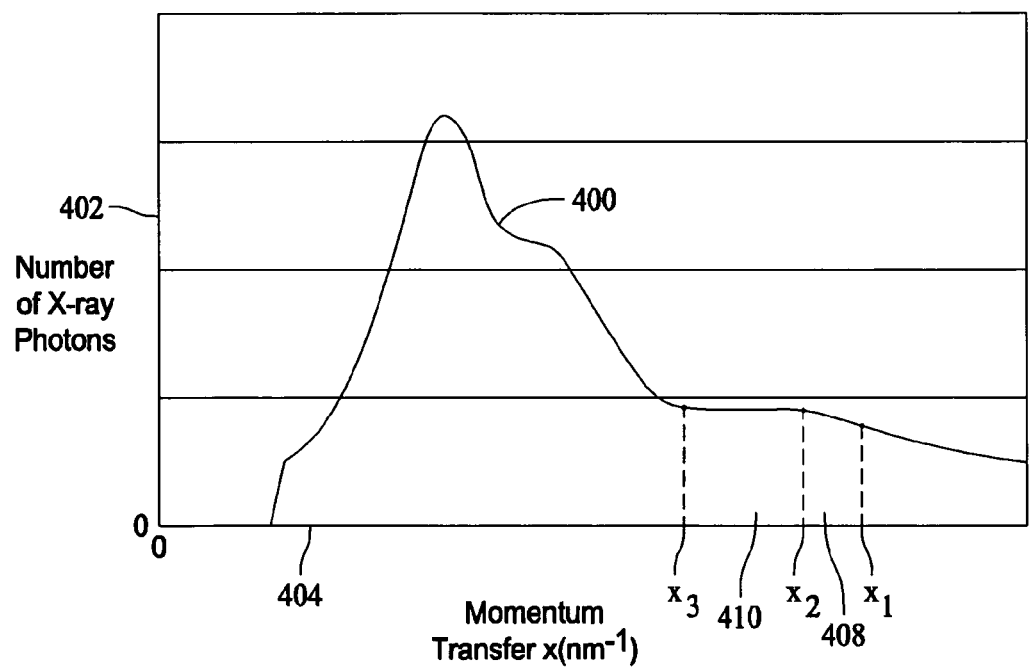
FIG. 4 shows a diffraction profile generated by a processor of the system of FIG. 2.

FIG. 3 is a flowchart of an embodiment of a method for determining an atomic number of a substance and FIG. 4 shows a graph 400 or a diffraction profile D(x) generated 401 by processor 190. Graph 400 is a histogram having a plurality of intensity values at a plurality of momentum transfer values, such as $x_1$, $x_2$, and $x_3$, of the momentum transfer x. As an example, when an operating voltage of x-ray source 12 is 160 kilovolts, processor 190 calculates, by applying equation 1, an energy value $E_1$ of the energy E to be 160 keV, calculates, by applying equation 1, an energy value $E_2$ of the energy E to be 140 keV, and calculates, by applying equation 1, an energy value $E_3$ of the energy value E to be photon energy 120 keV. In the example, the photon energy values $E_1$, $E_2$, and $E_3$ correspond, through equation 1, to $x_1$ of four inverse nanometers, $x_2$ of 3.5 inverse nanometers, and to $x_3$ of three inverse nanometers, respectively. Graph 400 represents a histogram of a number of x-ray photons detected by detector 18 versus the momentum transfer x of the x-ray photons. A number of x-ray photons detected by detector 18 is plotted along an ordinate 402 and the momentum transfer x is plotted along an abscissa 404. As an example, abscissa 404 extends from and includes zero inverse nanometers to at most 10 inverse nanometers. An example of a total number of bins of numbers of x-ray photons plotted on ordinate 402 lies between 64 and 1024. An example of a number of x-ray photons detected by detector 18 per examination lies between 1000 and 100,000.

The diffraction profile ranging from $x \geqq 3$ $nm^{-1}$ is dominated by coherent scatter from free atoms of substance 42. In a tip region, extending from $x_1$ to $x_3$, of graph 400, an intensity of the scattered radiation is proportional to a product of density, such as a mean density, of substance 42 and a power, such as ranging between 2.5 and 3.5, of a mean atomic number of a plurality of materials within substance 42.

A cumulative number of x-ray photons that are scattered with momentum transfer values between $x_1$ and $x_2$ are represented within a band 408 under graph 400. Processor 190 determines a cumulative number of x-ray photons within band 408 by cumulatively summing a number of x-ray photons between momentum transfer values $x_1$ and $x_2$ on abscissa 404. A cumulative number of x-ray photons that are scattered with momentum transfer values between $x_2$ and $x_3$ are located within a band 410 under graph 400. Processor 190 determines a cumulative number of x-ray photons within band 410 by cumulatively summing a number of x-ray photons between momentum transfer values $x_2$ and $x_3$ on abscissa 404.

Figure 5:
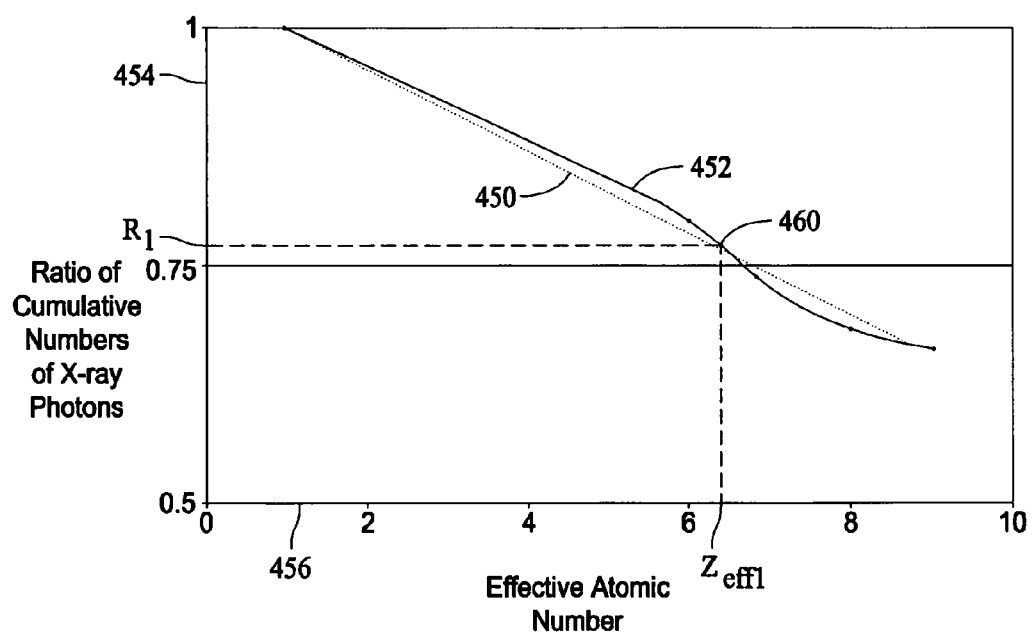
FIG. 5 shows a dotted line and a solid curve generated by the processor of the system of FIG. 2.

FIG. 5 shows a dotted line 450 and a solid curve 452 generated by processor 190. Solid curve 452 represents a theoretical relationship between a ratio of total or cumulative scatter cross-sections and an atomic number Z. As an example, processor 190 plots solid curve 452 from an example of the theoretical relationship mentioned in Hubbell, J. H., Veigele, W. J., Briggs, E. A., Brown, R. T., Cromer, D. T., Howerton, R. J., Atomic Form Factors, Incoherent Scattering Functions and Photon Scattering Cross-sections, Journal of Physics and Chemical Reference Data, Volume 4, page 471 (1975), Erratum: Atomic Form Factors, Incoherent Scattering Functions, and Photon Scattering Cross Sections, Journal of Physics and Chemical Reference Data, Volume 6, page 615 (1977). As another example, the theoretical relationship includes an atomic number value of oxygen as eight corresponding to a ratio of 0.68 of total scatter cross-sections calculated for oxygen. As yet another example, the theoretical relationship includes an atomic number value of carbon as six corresponding to a ratio of 0.73 of total scatter cross-sections calculated from carbon. As still another example, processor 190 calculates a ratio of a total scatter cross-section of hydrogen at the momentum transfer value $x_3$ and a total scatter cross-section of hydrogen at the momentum transfer value $x_2$, and plots the ratio on solid curve 452. As another example, processor 190 calculates a ratio of a total scatter cross-section of flourine at the momentum transfer value $x_2$ and a total scatter cross-section of flourine at the momentum transfer value $x_1$ and plots the ratio on solid curve 452. As yet another example, processor 190 calculates a ratio of a total scatter cross-section of carbon at the momentum transfer value $x_2$ and a total scatter cross-section of carbon at the momentum transfer value $x_1$, and plots the ratio on solid curve 452. Processor 190 generates dotted line 450 as a linear fit or linear regression to the theoretical relationship.

A plurality of ratios of total scatter cross-sections are plotted along an ordinate 454 and a plurality of atomic numbers Z are measured along an abscissa 456. For example, a plurality of atomic number values on dotted line 450 extend from an atomic number one of hydrogen to an atomic number nine of flourine and a plurality of ratios of total scatter cross-sections evaluated at momentum transfer values within a first set of regions of bands 408 and 410 and total scatter cross-sections evaluated at momentum transfer values within a second set of regions of bands 408 and 410.

Processor 190 calculates a ratio of cumulative numbers of x-ray photons within bands 408 and 410. For example, processor 190 determines that $R_1$ is a ratio of a cumulative number of x-ray photons within band 408 to a cumulative number of x-ray photons within band 410. Processor 190 determines 458, by using the solid curve 452, an effective atomic number $Z_{eff}$ corresponding to a ratio of a cumulative number of x-ray photons within band 408 and a cumulative number of x-ray photons within band 410. As an example, processor 190 perpendicularly extends a horizontal line from the ratio $R_1$ to intersect solid curve 452 at an intersection point 460 and extends a line from intersection point 460 to perpendicularly intersect abscissa 456 at an effective atomic number value $Z_{eff1}$. Alternatively, processor 190 determines, by using the dotted line 450, the effective atomic number $Z_{eff}$ corresponding to a ratio of a cumulative number of x-ray photons within band 408 and a cumulative number of x-ray photons within band 410. As an example, processor 190 perpendicularly extends a horizontal line from the ratio $R_1$ to intersect dotted line 450 at an intersection point and extends a line from the intersection point to perpendicularly intersect abscissa 456 at an effective atomic number value $Z_{eff2}$.

Processor 190 determines a type or a kind, such as uranium, carbon, oxygen, or plutonium, of substance 42 based on the effective atomic number $Z_{eff}$, such as $Zeff_1$, determined from a ratio of cumulative numbers of x-ray photons. For example, processor 190 determines that substance 42 is carbon upon determining that an effective atomic number value 6 corresponds to a ratio of 0.73 of cumulative numbers of x-ray photons detected by detector 18. Alternatively, processor 190 determines a type or a kind, such as uranium, carbon, oxygen, or plutonium, of substance 42 based on the effective atomic number value $Zeff_2$ determined from a ratio of cumulative numbers of x-ray photons.

Technical effects of the herein described systems and methods for determining an atomic number of a substance include determining the effective atomic number $Z_{eff}$ of substance 42 to identify a kind of substance 42. Other technical effects include determining whether substance 42 generates a dark alarm and determining whether substance 42 is a special nuclear material. The dark alarm is generated when substance 42 includes a high attenuating material, such as a metal. When substance 42 includes the high attenuating material, it is difficult for low energy x-ray quanta to pass through substance 42 to perform an analysis of a diffraction profile of substance 42. Yet other technical effects include using energy region 412 within the high-attenuating region to identify a slurry explosive or alternatively a gel explosive and to reduce a false alarm rate.

While the invention has been described in terms of various specific embodiments, those skilled in the art will recognize that the invention can be practiced with modification within the spirit and scope of the claims.

What is claimed is:

1. A method for determining a type of substance, said method comprising:
   determining a first number of coherent scatter x-ray photons in a first band of a diffraction profile;
   determining a second number of coherent scatter x-ray photons in a second band of the diffraction profile;
   calculating a measured ratio of the first number to the second number;
   determining an effective atomic number based on the measured ratio; and
   identifying the type of substance based on the effective atomic number.

2. A method in accordance with claim 1 wherein the substance comprises one of an amorphous substance, a quasi-amorphous substance, and a partially crystalline substance.

3. A method in accordance with claim 1 wherein the diffraction profile maps a cumulative number of photons versus a plurality of momentum transfer values, and wherein the plurality of momentum transfer values ranges from 0.5 inverse nanometers to ten inverse nanometers.

4. A method in accordance with claim 1 wherein the diffraction profile maps a cumulative number of photons versus a plurality of momentum transfer values, and wherein the plurality of momentum transfer values ranges from three inverse nanometers to four inverse nanometers.

5. A method in accordance with claim 1 further comprising:
   generating a theoretical relationship mapping a plurality of atomic numbers versus a plurality of ratios of total scatter cross-sections; and
   determining the effective atomic number corresponding to the measured ratio from the theoretical relationship.

6. A method in accordance with claim 1 further comprising:
   fitting a line to a theoretical relationship mapping a plurality of atomic numbers versus a plurality of ratios of total scatter cross-sections; and
   determining the effective atomic number corresponding to the measured ratio from the line.

7. A method in accordance with claim 1 further comprising generating the diffraction profile by receiving a plurality of energies of radiation scattered from the substance.

8. A processor for determining a type of substance, said processor configured to:
   determine a first number of coherent scatter x-ray photons in a first band of a diffraction profile;
   determine a second number of coherent scatter x-ray photons in a second band of the diffraction profile;
   calculate a measured ratio of the first number to the second number;
   determine an effective atomic number based on the measured ratio; and
   identify the type of substance based on the effective atomic number.

9. A processor in accordance with claim 8 wherein the substance comprises one of an amorphous substance, a quasi-amorphous substance, and a partially crystalline substance.

10. A processor in accordance with claim 8 further configured to generate the diffraction profile by mapping a cumulative number of photons versus a plurality of momentum transfer values, wherein the plurality of momentum transfer values range from 0.5 inverse nanometers to ten inverse nanometers.

11. A processor in accordance with claim 8 further configured to generate the diffraction profile by mapping a cumulative number of photons versus a plurality of momentum transfer values, and wherein the plurality of momentum transfer values range from three inverse nanometers to four inverse nanometers.

12. A processor in accordance with claim 8 further configured to:
   receive a theoretical relationship mapping a plurality of atomic numbers versus a plurality of ratios of total scatter cross-sections; and
   determine the effective atomic number corresponding to the measured ratio from the theoretical relationship.

13. A processor in accordance with claim 8 further configured to:

fit a line to a theoretical relationship mapping a plurality of atomic numbers versus a plurality of ratios of total scatter cross-sections; and determine the effective atomic number corresponding to the measured ratio from the line.

14. A processor in accordance with claim 8 further configured to generate the diffraction profile by receiving a plurality of energies of radiation scattered from the substance.

15. A system for determining a type of substance, said system comprising:

an x-ray source configured to generate x-rays;

a detector configured to detect primary and coherent scatter after the x-rays pass through the substance; and a processor configured to:

determine a first number of coherent scatter x-ray photons in a first band of a diffraction profile;

determine a second number of coherent scatter x-ray photons in a second band of the diffraction profile;

calculate a measured ratio of the first number to the second number;

determine an effective atomic number based on the measured ratio; and identify the type of substance based on the effective atomic number.

16. A system in accordance with claim 15 wherein the substance comprises one of an amorphous substance, a quasi-amorphous substance, and a partially crystalline substance.

17. A system in accordance with claim 15 wherein said processor is further configured to generate the diffraction profile by mapping a cumulative number of photons versus a plurality of momentum transfer values, wherein the plurality of momentum transfer values range from 0.5 inverse nanometers to ten inverse nanometers.

18. A system in accordance with claim 15 wherein said processor is further configured to generate the diffraction profile by mapping a cumulative number of photons versus a plurality of momentum transfer values, and wherein the plurality of momentum transfer values range from three inverse nanometers to four inverse nanometers.

19. A system in accordance with claim 15 wherein said processor is further configured to:

receive a theoretical relationship mapping a plurality of atomic numbers versus a plurality of ratios of total scatter cross-sections; and determine the effective atomic number corresponding to the measured ratio from the theoretical relationship.

20. A system in accordance with claim 15 wherein said processor is further configured to:

fit a line to a theoretical relationship mapping a plurality of atomic numbers versus a plurality of ratios of total scatter cross-sections; and determine the effective atomic number corresponding to the measured ratio from the line.

* * * * *